(12) United States Patent
Rao et al.

(10) Patent No.: US 9,000,158 B2
(45) Date of Patent: Apr. 7, 2015

(54) PROCESS FOR PREPARING LEVOSIMENDAN AND INTERMEDIATES FOR USE IN THE PROCESS

(75) Inventors: Dharmaraj Ramachandra Rao, Maharashtra (IN); Rajendra Narayanrao Kankan, Maharashtra (IN); Manjinder Singh Phull, Maharashtra (IN); Ashwini Amol Sawant, Maharashtra (IN)

(73) Assignee: Cipla Limited, Mumbai (IN)

( * ) Notice: Subject to any disclaimer, the term of this patent is extended or adjusted under 35 U.S.C. 154(b) by 47 days.

(21) Appl. No.: 13/384,211

(22) PCT Filed: Jul. 12, 2010

(86) PCT No.: PCT/GB2010/001325
§ 371 (c)(1),
(2), (4) Date: Mar. 19, 2012

(87) PCT Pub. No.: WO2011/007123
PCT Pub. Date: Jan. 20, 2011

(65) Prior Publication Data
US 2012/0165524 A1    Jun. 28, 2012

(30) Foreign Application Priority Data
Jul. 14, 2009 (IN) .................. 1645/MUM/2009

(51) Int. Cl.
C07D 237/14    (2006.01)
C07D 237/04    (2006.01)

(52) U.S. Cl.
CPC .................. C07D 237/04 (2013.01)

(58) Field of Classification Search
USPC ....................................... 544/239
See application file for complete search history.

(56) References Cited

U.S. PATENT DOCUMENTS

| | | |
|---|---|---|
| 5,569,657 A | 10/1996 | Nore et al. |
| 6,180,789 B1 | 1/2001 | Timmerbacka et al. |

FOREIGN PATENT DOCUMENTS

| | | |
|---|---|---|
| CN | 1616437 A | 5/2005 |
| EP | 0208518 B1 | 9/1991 |
| JP | 10109977 A | 4/1998 |
| JP | 2001517702 A | 10/2001 |
| JP | 200923978 A | 2/2009 |
| WO | 9212135 A1 | 7/1992 |
| WO | 9735841 A2 | 10/1997 |
| WO | 9916443 A1 | 4/1999 |
| WO | 2008107911 A2 | 9/2008 |

OTHER PUBLICATIONS

Foreign communication from the priority application—International Search Report and Written Opinion, PCT/GB2010/001325, 15 pages, Sep. 23, 2010.
Foreign communication from a related counterpart application—English Translation of Japanese Office Action, Japanese Application No. 2012-520083, Jul. 31, 2014, 2 pages.

Primary Examiner — James O Wilson
Assistant Examiner — Cecilia M Jaisle
(74) Attorney, Agent, or Firm — Conley Rose, P.C.; Rodney B. Carroll

(57) ABSTRACT

In an embodiment, the present invention provides a process for preparing (−)-6-(4-aminophenyl)-5-methylpyridazin-3-(2H)-one, which process comprises: a) reacting racemic 6-(4-aminophenyl)-4,5-dihydro-5-methyl-3-(2H)-pyridazinone of formula II

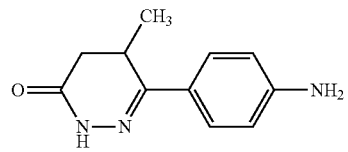

Formula II with a chiral tartaric acid derivative to obtain a diastereomeric salt of (−)-6-(4-aminophenyl)-4,5-dihydro-5-methyl-3-(2H)-pyridazinone and the chiral tartaric acid derivative; and b) reacting the diastereomeric salt with a base to obtain (−)-6-(4-aminophenyl)-4,5-dihydro-5-methyl-3-(2H)-pyridazinone. The (−)-6-(4-aminophenyl)-4,5-dihydro-5-methyl-3-(2H)-pyridazinone may be used to prepare levosimendan.

12 Claims, No Drawings

PROCESS FOR PREPARING LEVOSIMENDAN AND INTERMEDIATES FOR USE IN THE PROCESS

CROSS-REFERENCE TO RELATED APPLICATIONS

This application is a filing under 35 U.S.C. 371 of International Application No. PCT/GB2010/001325 filed Jul. 12, 2010, entitled "Process for Preparing of Levosimendan and Intermediates for use in the Process," claiming priority of Indian Patent Application No. 1645/MUM/2009 filed Jul. 14, 2009, which applications are incorporated by reference herein in their entirety.

FIELD OF INVENTION

The present invention relates to a process for preparing the levo isomer of [[4-(1,4,5,6-tetrahydro-4-methyl-6-oxo-3-pyridazinyl)phenyl]hydrazono]propanedinitrile (levosimendan), which is represented by the following structure.

Formula I

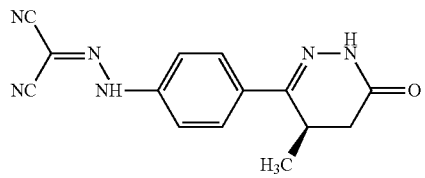

BACKGROUND

Levosimendan is a highly potent cardiotonic that increases the sensitivity of the heart to calcium without causing a rise in intracellular calcium. The drug is marketed by Abbott under the trade name Simdax. It was first disclosed in U.S. Pat. No. 5,569,657.

The prior art indicates that pure levosimendan can be obtained by passing the racemic mixture over a chiral phase chromatography column. But the process becomes tedious and industrially unacceptable when a large quantity of material is involved.

One prior art technique involves using the optically-pure (−)-enantiomer of 6-(4-aminophenyl)-5-methylpyridazin-3-(2H)-one as starting material. The method of obtaining (−)-6-(4-aminophenyl)-5-methylpyridazin-3-(2H)-one is given in EP208518, which describes the separation of pure enantiomers of 6-(4-aminophenyl)-4,5-dihydro-5-methyl-3-(2H)-pyridazinone using a chiral HPLC column.

CN1616437 describes treating (+)-6-(4-aminophenyl)-4,5-dihydro-5-methyl-3-(2H)-pyridazinone with 50% alkali or 50% acid.

JP10109977 discloses the use of 1-propanol/ethyl acetate as resolving solvent and L- or D-tartaric acid as resolving agent.

U.S. Pat. No. 5,569,657 discloses the preparation of levosimendan and its salts. (±)-6-(4-aminophenyl)-5-methylpyridazin-3-(2H)-one is dissolved in 2-propanol on heating. L-tartaric acid is gradually added to the solution and stirred on heating to obtain a clear solution. The solution is cooled slowly to room temperature and then stirred overnight at 200 C to obtain a crystalline product. On filtering, the wet salt is dissolved in water and to it potassium carbonate solution is added with stirring. The free base obtained is filtered, washed with water and dried. The product is further dissolved in dioxane on heating and allowed to cool to room temperature. The contents are filtered and dried under vacuum to obtain (−)-6-(4-aminophenyl)-5-methylpyridazin-3-(2H)-one crystalline solid. The pure (−)-6-(4-aminophenyl)-5-methylpyridazin-3-(2H)-one compound is then treated with sodium nitrite and malononitrile under acidic condition to obtain levosimendan. A disadvantage of the resolution process disclosed is that to obtain a high optical purity (99.5%) of the pyridazinone compound, recrystallisation with dioxane is required. Also the process involves multiple steps and is time consuming.

U.S. Pat. No. 6,180,789 describes the preparation of levosimendan by treating the (−)-enantiomer of 6-(4-amino phenyl)-5-methylpyridazin-3-(2H)-one, resolved using D- or L-tartaric acid in aqueous ethyl acetate, with sodium nitrite and malononitrile and further crystallizing with aqueous acetone. The patent also discloses other resolving agents such as benzoic acid, sulphuric acid, and resolving solvents such as isopropanol, isobutanol, isopropyl acetate, butyl acetate, acetone and acetonitrile. These conditions are said to cause partial resolution only.

There are certain drawbacks of the process disclosed in U.S. Pat. No. 6,180,789—

When D-tartaric acid is the resolving agent—
  Excess amount of resolving agent is required to achieve complete resolution.
  Seeding with D-tartaric acid salt of (−)-6-(4-amino phenyl)-5-methylpyridazin-3-(2H)-one is also needed in the process.
  Hot filtration of the precipitate is to be done; which is not at all workable when dealing with large batches at industrial scale.
  The temperature of reaction is to be maintained at 0° C.
  The enantiomeric purity of the product is low, even after giving a number of washings.
  In order to obtain the desired enantiomeric excess, it is necessary to perform recrystallisation with acetonitrile in the presence of absorbent followed by washing with excess acetonitrile. Treatment with a large amount of solvent increases the cost of process and also reduces the yield due to wastage.

When L-tartaric acid is the resolving agent—
  For the precipitation of salt, cooling up to −10° C. is required.
  The enantiomeric purity of the desired (−)-6-(4-amino phenyl)-5-methylpyridazin-3-(2H)-one product is quite low (78.7%).

Due to the problems with the prior art there is felt a need to develop a new process for resolving levosimendan that is simple, economical, eco-friendly and high-yielding.

SUMMARY OF THE INVENTION

According to a first aspect of the present invention, there is provided a process for preparing (−)-6-(4-aminophenyl)-5-methylpyridazin-3-(2H)-one, which process comprises: a) reacting racemic 6-(4-aminophenyl)-4,5-dihydro-5-methyl-3-(2H)-pyridazinone with a resolving agent, preferably a chiral tartaric acid derivative, typically in the presence of a solvent; and b) isolating the (−)-6-(4-aminophenyl)-4,5-dihydro-5-methyl-3-(2H)-pyridazinone.

In an embodiment, step a) results in a diastereomeric salt which is a salt of (−)-6-(4-aminophenyl)-4,5-dihydro-5-methyl-3-(2H)-pyridazinone and the chiral tartaric acid derivative. The (+)-6-(4-aminophenyl)-4,5-dihydro-5-methyl-3-

(2H)-pyridazinone is present in the mother liquor of the reaction mass, whereas the salt precipitates therefrom. In this embodiment, the process comprises: a) reacting racemic 6-(4-aminophenyl)-4,5-dihydro-5-methyl-3-(2H)-pyridazinone of formula II with the chiral tartaric acid derivative to obtain the diastereomeric salt of (−)-6-(4-aminophenyl)-4,5-dihydro-5-methyl-3-(2H)-pyridazinone and the chiral tartaric acid derivative; and b) reacting the diastereomeric salt with a base to obtain (−)-6-(4-aminophenyl)-4,5-dihydro-5-methyl-3-(2H)-pyridazinone. In this embodiment, the chiral acid derivative may be di-p-anisoyl-D-tartaric acid.

In an alternative embodiment, step a) results in a diastereomeric salt which is a salt of (+)-6-(4-aminophenyl)-4,5-dihydro-5-methyl-3-(2H)-pyridazinone and the chiral tartaric acid derivative. The (−)-6-(4-aminophenyl)-4,5-dihydro-5-methyl-3-(2H)-pyridazinone is present in the mother liquor of the reaction mass, whereas the salt precipitates therefrom. In this embodiment, the process comprises: a) reacting racemic 6-(4-aminophenyl)-4,5-dihydro-5-methyl-3-(2H)-pyridazinone of formula II with the chiral tartaric acid derivative to obtain the diastereomeric salt of (−)-6-(4-aminophenyl)-4, 5-dihydro-5-methyl-3-(2H)-pyridazinone and the chiral tartaric acid derivative; and b) isolating the (−)-6-(4-aminophenyl)-4,5-dihydro-5-methyl-3-(2H)-pyridazinone from the mother liquor. In this embodiment, the chiral acid derivative may be di-p-anisoyl-L-tartaric acid.

In an embodiment, the chiral tartaric acid derivative is selected from the D- or L-isomer of di-p-anisoyl-tartaric acid, di-p-tolyl-tartaric acid or O, O'-dibenzoyl-tartaric acid. Preferably, the chiral acid is the D-isomer of the tartaric acid derivative. Preferably, the chiral tartaric acid derivative is di-p-anisoyl-D-tartaric acid. Most preferably, the chiral tartaric acid derivative is di-p-anisoyl-D-tartaric acid.

In an embodiment, the solvent employed for resolution, i.e. in step (a), is a mixture of water and a polar solvent. The polar solvent may be selected from methanol, ethanol, isopropanol, n-butanol, acetone and acetonitrile. Preferably, a mixture of water and ethanol is used.

The above process may further comprise converting the (−)-6-(4-aminophenyl)-5-methylpyridazin-3-(2H)-one to levosimendan. The conversion may comprise reacting (−)-6-(4-aminophenyl)-4,5-dihydro-5-methyl-3-(2H)-pyridazinone with sodium nitrite and malononitrile. In an embodiment, the process of the present invention yields levosimendan in substantially-pure enantiomeric form. Preferably, the ratio of the levo-isomer:dextro-isomer prepared by the process of present invention is about 99:1. Preferably, the levosimendan prepared from the present process has a purity of about 99.9%, as determined by chiral HPLC.

According to another aspect of the present invention, there is provided the salt of (−)-6-(4-aminophenyl)-5-methylpyridazin-3-(2H)-one and di-p-anisoyl-D-tartaric acid. This compound has the formula VI shown below.

Formula VI

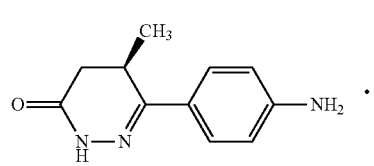

According to another aspect of the present invention, there is provided the salt of (+)-6-(4-aminophenyl)-5-methylpyridazin-3-(2H)-one and di-p-anisoyl-L-tartaric acid. This compound has the formula VII as shown below.

Formula VII

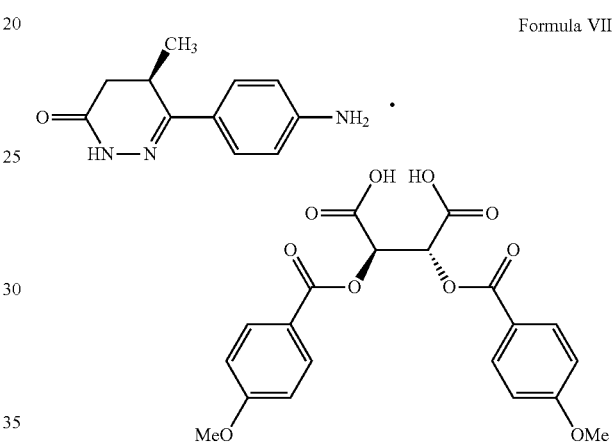

A preferred chiral tartaric acid derivative for use in the process of the present invention is di-p-anisoyl-tartaric acid, and compounds of formula VI and VII are the corresponding preferred products of step a) of the process of the present invention when di-p-anisoyl-tartaric acid is the resolving agent. Compounds VI and VII are, therefore, highly-advantageous intermediates for use in the process of the present invention.

According to another aspect of the present invention, there is provided a process for preparing a compound of formula VI, which process comprises reacting racemic 6-(4-aminophenyl)-4,5-dihydro-5-methyl-3-(2H)-pyridazinone with di-p-anisoyl-D-tartaric acid.

According to another aspect of the present invention, there is provided a process which comprises: (i) reacting racemic 6-(4-aminophenyl)-4,5-dihydro-5-methyl-3-(2H)-pyridazinone of formula II Formula II

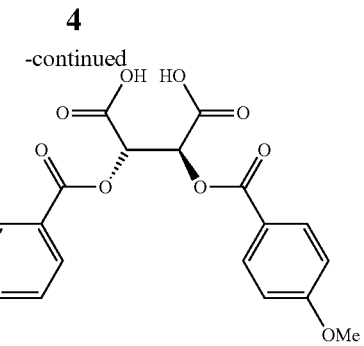

with a chiral tartaric acid derivative to obtain the diastereomeric salt of (−)-6-(4-aminophenyl)-4,5-dihydro-5-methyl-3-(2H)-pyridazinone and the chiral tartaric acid derivative and a mother liquor enriched in (+)-6-(4-aminophenyl)-4,5-dihydro-5-methyl-3-(2H)-pyridazinone; (ii) converting (+)-6-(4-aminophenyl)-4,5-dihydro-5-methyl-3-(2H)-pyridazinone obtained from step (i) to racemic 6-(4-aminophenyl)-4,5-dihydro-5-methyl-3-(2H)-pyridazinone; and (iii) employing racemic 6-(4-aminophenyl)-4,5-dihydro-5-methyl-3-(2H)-pyridazinone obtained from step (ii) in a process as described above.

According to another aspect of the present invention, there is provided (−)-6-(4-aminophenyl)-4,5-dihydro-5-methyl-3-(2H)-pyridazinone prepared according to any one of the processes described above.

According to another aspect of the present invention, there is provided levosimendan prepared according to any one of the processes described above.

According to another aspect of the present invention, there is provided a pharmaceutical composition comprising levosimendan prepared according to any one of the processes described above together with one or more pharmaceutically acceptable excipients.

DESCRIPTION

The invention will now be described in detail in connection with certain preferred and optional embodiments, so that various aspects thereof may be more fully understood and appreciated.

The process of present invention relates to the preparation of levosimendan in high optical purity without any recrystallisation or purification.

In an embodiment, there is provided a process for preparing levosimendan by resolving racemic 6-(4-aminophenyl)-4,5-dihydro-5-methyl-3-(2H)-pyridazinone with a resolving agent to obtain the diastereomeric salt of (−)-6-(4-aminophenyl)-4,5-dihydro-5-methyl-3-(2H)-pyridazinone and the resolving agent, converting the salt into (−)-6-(4-aminophenyl)-4,5-dihydro-5-methyl-3-(2H)-pyridazinone and then treating the free base with sodium nitrite and malononitrile.

In an embodiment, the process of the present invention comprises resolution of racemic 6-(4-aminophenyl)-4,5-dihydro-5-methyl-3-(2H)-pyridazinone of formula II with a resolving agent which is a chiral tartaric acid derivative, preferably of formula III, in the presence of a solvent to obtain the corresponding diastereomeric salt of formula IV.

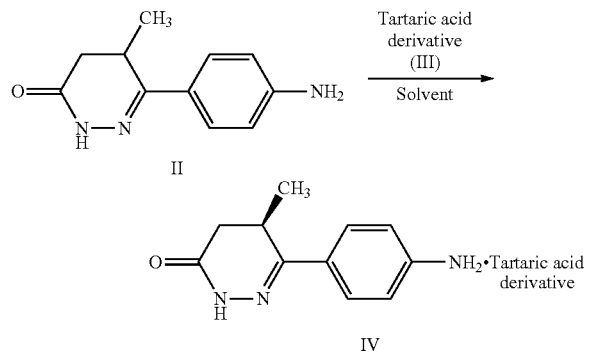

The chiral tartaric acid derivative is selected from the D- or L-isomer of di-p-anisoyl-tartaric acid, di-p-tolyl-tartaric acid or O,O'-dibenzoyl-tartaric acid. Preferably, the chiral acid for the process of present invention is the D-isomer of the tartaric acid derivative. Most preferably, di-p-anisoyl-D-tartaric acid of formula III is used.

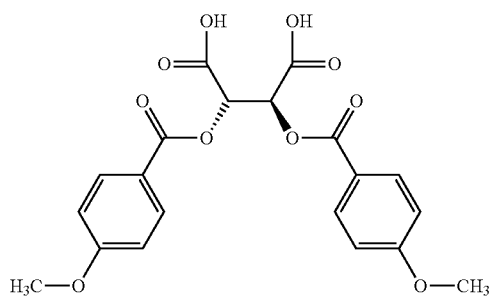

The solvent employed for the preparation of the diastereomeric salt in the process of present invention is preferably a mixture of water and a polar solvent. The polar solvent may be selected from the group consisting of methanol, ethanol, isopropanol, n-butanol, acetone and acetonitrile. Most preferably, the solvent used in the resolution step is a mixture of water and ethanol.

In another embodiment, the process of the present invention further involves treating the diastereomeric salt of formula IV with a base to obtain (−)-6-(4-aminophenyl)-4,5-dihydro-5-methyl-3-(2H)-pyridazinone of formula V.

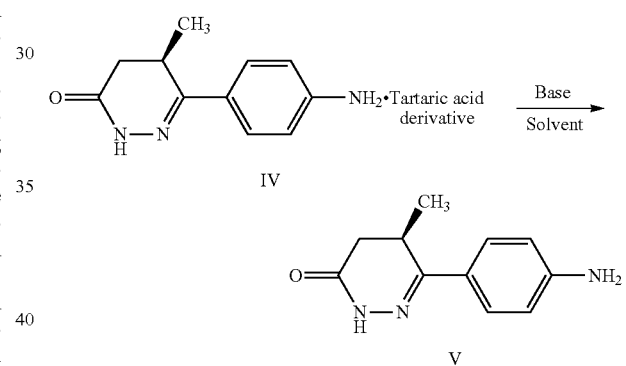

The base used may be an organic or inorganic base, for example selected from ammonia, sodium methoxide, sodium hydroxide, potassium hydroxide, sodium carbonate, potassium bicarbonate, potassium carbonate or sodium bicarbonate.

In another aspect of the present invention, (−)-6-(4-aminophenyl)-4,5-dihydro-5-methyl-3-(2H)-pyridazinone (V), suitably as prepared by the above process, is treated with sodium nitrite and malononitrile to obtain levosimendan (I).

In an embodiment, the particularly preferred process of present invention for preparing levosimendan (formula I) comprises:

(a) resolving racemic 6-(4-aminophenyl)-4,5-dihydro-5-methyl-3-(2H)-pyridazinone of Formula II,

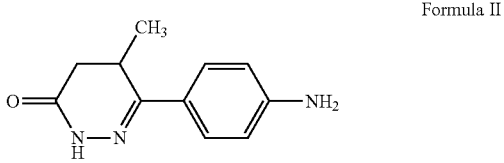

with di-p-anisoyl-D-tartaric acid of formula III in the presence of a mixture of water and ethanol to form the diastereomeric (−)-6-(4-aminophenyl)-4,5-dihydro-5-methyl-3-(2H)-pyridazinone di-p-anisoyl-D-tartaric acid salt of formula VI,

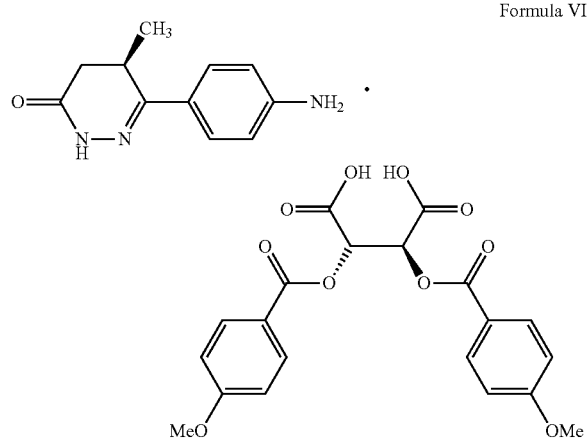

Formula VI typically at a temperature ranging from 55° C. to 70° C.;

(b) treating the diastereomeric salt of formula VI with an organic or inorganic base selected from ammonia, sodium methoxide, sodium hydroxide, potassium hydroxide, sodium carbonate, potassium bicarbonate, potassium carbonate or sodium bicarbonate to obtain the (−)-isomer of 6-(4-aminophenyl)-4,5-dihydro-5-methyl-3-(2H)-pyridazinone of formula V;

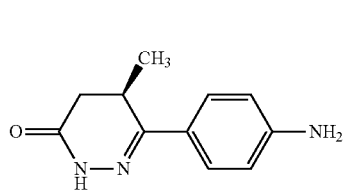

Formula V (c) reacting (−)-6-(4-aminophenyl)-4,5-dihydro-5-methyl-3-(2H)-pyridazinone of formula V with sodium nitrite and malononitrile under acidic conditions to obtain levosimendan of formula I.

The salt formed in step (a) may further be optionally recrystallised using a water and ethanol solvent mixture.

The mother liquor from the resolution step (a) is enriched with (+)-6-(4-aminophenyl)-4,5-dihydro-5-methyl-3-(2H)-pyridazinone and may be converted into (±)-6-(4-aminophenyl)-4,5-dihydro-5-methyl-3-(2H)-pyridazinone and used again in the process of the present invention.

The process of present invention yields levosimendan in highly-pure enantiomeric form. The ratio of levosimendan:dextrosimendan as prepared by the process of present invention is typically about 99:1, as compared to the 96:4 ratio obtained by prior art processes. Also the levosimendan prepared from the present process typically has a purity of about 99.9%, as determined by chiral HPLC.

In another embodiment, the L-isomer of di-p-anisoyl-tartaric acid may be used. For example, racemic 6-(4-aminophenyl)-4,5-dihydro-5-methyl-3-(2H)-pyridazinone is reacted with di-p-anisoyl-L-tartaric acid in the presence of a water and ethanol solvent mixture to form the diastereomeric (+)-6-(4-aminophenyl)-4,5-dihydro-5-methyl-3-(2H)-pyridazinone di-p-anisoyl-L-tartaric acid salt. The mother liquor obtained on resolution contains (−)-6-(4-aminophenyl)-4,5-dihydro-5-methyl-3-(2H)-pyridazinone which may act as starting material for the preparation of levosimendan. The precipitated product may be used in the process of the present invention for recycling the In the process of the present invention, highly-pure (−)-6-(4-aminophenyl)-4,5-dihydro-5-methyl-3-(2H)-pyridazinone is obtained without any recrystallisation or purification. Thus, preventing the wastage of solvent and corresponding decrease in yield of product; in turn making the process economical, high-yielding and industrially-viable. Also, the preferred use of di-p-anisoyl-D-tartaric acid as resolving agent causes rapid precipitation of the diastereomeric salt which in turn in a single step gives levosimendan in high yield. The solvent employed in the process of present invention is preferably a mixture with water which makes the process environmentally-friendly.

EXAMPLES

The details of the invention are given in the examples which are provided below for illustration only and therefore these examples should not be construed to limit the scope of the invention.

Example 1

Step 1

50 g of racemic 6-(4-aminophenyl)-4,5-dihydro-5-methyl-3-(2H)-pyridazinone and 500 ml ethanol were added to a flask and stirred at 65° C. for 30 minutes. Further di-p-anisoyl-D-tartaric acid (113.3 g) and 500 ml water were added and stirring was continued for 1 hour. The reaction mass was cooled to 15° C. and stirred for another 30 minutes. Then the mass was filtered, washed with water and dried under vacuum at 55° C. to obtain the corresponding diastereomeric salt (yield—110 g, purity—99.5%).

Step 2

The obtained salt and water (500 ml) were added to a reaction vessel and stirred at 25-30° C. for 30 minutes. The pH of the resulting solution was adjusted to 8-9 by adding ammonia solution and stirring was continued for 30 minutes. After completion of reaction, the contents were filtered and dried under vacuum at 55° C. to obtain solid (−)-6-(4-aminophenyl)-4,5-dihydro-5-methyl-3-(2H)-pyridazinone (yield—24 g, purity—99.6%).

Step 3

To a solution of (−)-6-(4-aminophenyl)-4,5-dihydro-5-methyl-3-(2H)-pyridazinone (20 g) and dilute hydrochloric acid (52 ml of concentrated hydrochloric acid in 789 ml of water), 8 g of dilute sodium nitrite (8 g of sodium nitrite in 52 ml of water) was added and stirred. After 10 minutes, malononitrile solution (6.3 g malononitrile in 52 ml of water) was added. The solution was stirred for 1 hour at room temperature. The pH of the suspension was adjusted to 6.0 with sodium acetate solution. The suspension was filtered, washed with water followed by ethanol and then dried to obtain solid levosimendan (yield—22 g, purity—99.9%).

Example 2

10 g of racemic 6-(4-aminophenyl)-4,5-dihydro-5-methyl-3-(2H)-pyridazinone and 100 ml ethanol were added and stirred at 65° C. for 30 minutes. Di-p-anisoyl-L-tartaric acid (22.6 g) and 100 ml water were added and stirring continued for 1 hour. After completion of reaction, the mass was cooled to 15° C. to obtain a solid and then filtered. The mother liquor obtained was concentrated to remove ethanol then basified with ammonia. The precipitated solid was filtered and treated with sodium nitrite and malononitrile as described above to obtain solid levosimendan (yield—4 g, purity—99.6%).

Example 3

25 g of (+)-6-(4-aminophenyl)-4,5-dihydro-5-methyl-3-(2H)-pyridazinone, obtained from step 1 of Example 1, and 50% sodium hydroxide solution were heated at 90° C. The reaction mass was cooled to room temperature, filtered and washed with water. The solid obtained was charged in a flask along with 250 ml ethanol and stirred at 65° C. for 30 minutes. Di-p-anisoyl-D-tartaric acid (56.6 g) and 250 ml water were added and stirring was continued for 1 hour. The reaction mass was cooled to 15° C. and stirred for another 30 minutes. The reaction mass was filtered and washed with water. The wet solid diastereomeric salt was charged in a round bottom flask along with water and the contents stirred at 25° C. To this mixture, 10% potassium carbonate was added and the pH was adjusted to 8-9. The reaction mass was stirred for 30 minutes and then filtered. The solid obtained was treated with sodium nitrite and malononitrile solution in presence of dilute hydrochloric acid to obtain levosimendan ((yield—10.5 g, purity—99.5%).

It will be appreciated that the invention may be modified within the scope of the appended claims.

The invention claimed is:

1. A process for preparing (−)-6-(4-aminophenyl)-4,5-dihydro-5-methyl-3-(2H)-pyridazinone, which process comprises:
   a) reacting racemic 6-(4-aminophenyl)-4,5-dihydro-5-methyl-3-(2H)-pyridazinone of formula II

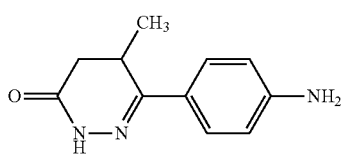

Formula II with a chiral tartaric acid derivative to form a first diastereomer salt and a second diastereomer salt, wherein the first diastereomer salt is a salt of (−)-6-(4-aminophenyl)-4,5-dihydro-5-methyl-3-(2H)-pyridazinone and the chiral tartaric acid derivative, and wherein the second diastereomer salt is a salt of (+)-6-(4-aminophenyl)-4,5-dihydro-5-methyl-3-(2H)-pyridazinone and the chiral tartaric acid derivative; and
   b) isolating (−)-6-(4-aminophenyl)-4,5-dihydro-5-methyl-3-(2H)-pyridazinone from the first diastereomer salt, wherein the chiral tartaric acid derivative is selected from the D- or L-isomer of di-p-anisoyl-tartaric acid, di-p-tolyl-tartaric acid or O,O'-dibenzoyl-tartaric acid.

2. The process according to claim 1, wherein step b) comprises separating the first diastereomer salt from the second diastereomer salt and reacting the first diastereomer salt with an organic or inorganic base to obtain (−)-6-(4-aminophenyl)-4,5-dihydro-5-methyl-3-(2H)-pyridazinone.

3. The process according to claim 2, wherein the base is selected from the group consisting of ammonia, sodium methoxide, sodium hydroxide, potassium hydroxide, sodium carbonate, potassium bicarbonate, potassium carbonate and sodium bicarbonate.

4. The process according to claim 2, wherein the first diastereomer salt is a salt of (−)-6-(4-aminophenyl)-4,5-dihydro-5-methyl-3-(2H)-pyridazinone and di-p-anisoyl-D-tartaric acid having the formula VI Formula VI or a salt of (−)-6-(4-aminophenyl)-4,5-dihydro-5-methyl-3-(2H)-pyridazinone and di-p-anisoyl-L-tartaric acid having the formula VII Formula VII 5. The process according to claim 1, wherein step a) is carried out in the presence of a solvent, wherein the solvent is a mixture of water and a polar solvent.

6. The process according to claim 5, wherein the polar solvent is selected from the group consisting of methanol, ethanol, isopropanol, n-butanol, acetone and acetonitrile.

7. The process according to claim 5, wherein the solvent is a mixture of water and ethanol.

8. The process according to claim 1, wherein the chiral tartaric acid derivative is the D-isomer of the tartaric acid derivative.

9. The process according to claim 1, wherein the chiral tartaric acid derivative is di-p-anisoyl-D-tartaric acid.

10. A process for preparing levosimendan, which process comprises:
   a) reacting racemic 6-(4-aminophenyl)-4,5-dihydro-5-methyl-3-(2H)-pyridazinone of formula II

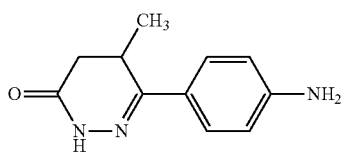

Formula II with a chiral tartaric acid derivative selected from the D- or L-isomer or di-p-anisoyl-tartaric acid, di-p-tolyl-tartaric acid or O,O'-dibenzoyl-tartaric acid to form a first diastereomer salt and a second diastereomer salt, wherein the first diastereomer salt is a salt of (−)-6-(4-aminophenyl)-4,5-dihydro-5-methyl-3-(2H)-pyridazinone and the chiral tartaric acid derivative, and wherein the second diastereomer salt is a salt of (+)-6-(4-aminophenyl)-4,5-dihydro-5-methyl-3-(2H)-pyridazinone and the chiral tartaric acid derivative;

b) isolating (−)-6-(4-aminophenyl)-4,5-dihydro-5-methyl-3-(2H)-pyridazinone from the first diastereomer salt;

c) and converting (−)-6-(4-aminophenyl)-4,5-dihydro-5-methyl-3-(2H)-pyridazinone to levosimendan by reacting (−)-6-(4-aminophenyl)-4,5-dihydro-5-methyl-3-(2H)-pyridazinone with sodium nitrite and malononitrile.

11. A process for preparing (−)-6-(4-aminophenyl)-4,5-dihydro-5-methyl-3-(2H)-pyridazinone, which process comprises:

(i) reacting racemic 6-(4-aminophenyl)-4,5-dihydro-5-methyl-3-(2H)-pyridazinone of formula II

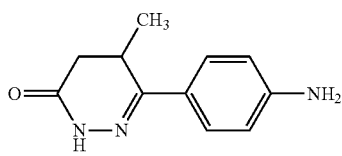

Formula II with a first chiral tartaric acid derivative selected from the D- or L-isomer of di-p-anisoyl-tartaric acid, di-p-tolyl-tartaric acid or O,O'-dibenzoyl-tartaric acid to obtain a first diastereomeric salt and a second diastereomeric salt, wherein the first diastereomeric salt is a salt of (−)-6-(4-aminophenyl)-4,5-dihydro-5-methyl-3-(2H)-pyridazinone and the first chiral tartaric acid derivative and wherein the second diastereomeric salt is a salt of a (+)-6-(4-aminophenyl)-4,5-dihydro-5-methyl-3-(2H)-pyridazinone and the first chiral tartaric acid derivative, and separating the first and second diastereomeric salts;

(ii) converting the (+)-6-(4-aminophenyl)-4,5-dihydro-5-methyl-3-(2H)-pyridazinone of the second diastereomeric salt obtained from step (i) to racemic 6-(4-aminophenyl)-4,5-dihydro-5-methyl-3-(2H)-pyridazinone; and (iii) reacting the racemic 6-(4-aminophenyl)-4,5-dihydro-5-methyl-3-(2H)-pyridazinone obtained from step (ii) with a second chiral tartaric acid derivative selected from the D- or L-isomer of di-p-anisoyl-tartaric acid, di-p-tolyl-tartaric acid or O,O'-dibenzoyl-tartaric acid to form a third diastereomeric salt and a fourth diastereomeric salt, wherein the third diastereomeric salt is a salt of (−)-6-(4-aminophenyl)-4,5-dihydro-5-methyl-3-(2H)-pyridazinone and the second chiral tartaric acid derivative, and wherein the fourth diastereomeric salt is a salt of (+)-6-(4-aminophenyl)-4,5-dihydro-5-methyl-3-(2H)-pyridazinone and the second chiral tartaric acid derivative; and (iv) isolating (−)-6-(4-aminophenyl)-4,5-dihydro-5-methyl-3-(2H)-pyridazinone from the third diastereomeric salt.

12. The process according to claim 11, wherein the step (ii) comprises reacting the (+)-6-(4-aminophenyl)-4,5-dihydro-5-methyl-3-(2H)-pyridazinone of the second diastereomeric salt with sodium hydroxide.

* * * * *